United States Patent [19]

Knollenberg

[11] Patent Number: 4,893,932
[45] Date of Patent: Jan. 16, 1990

[54] SURFACE ANALYSIS SYSTEM AND METHOD

[75] Inventor: Robert G. Knollenberg, Boulder, Colo.

[73] Assignee: Particle Measuring Systems, Inc., Boulder, Colo.

[21] Appl. No.: 262,216

[22] Filed: Oct. 21, 1988

Related U.S. Application Data

[63] Continuation of Ser. No. 859,054, May 2, 1986, abandoned.

[51] Int. Cl.$^4$ ............................................. G01N 21/01
[52] U.S. Cl. ................................... 356/369; 356/237; 356/338
[58] Field of Search ....................... 356/369, 237, 338

[56] References Cited

U.S. PATENT DOCUMENTS

| | | | |
|---|---|---|---|
| 3,502,888 | 3/1970 | Stites | 356/369 |
| 4,342,515 | 8/1982 | Akiha et al. | 356/237 |
| 4,469,442 | 9/1984 | Reich | 356/237 |
| 4,482,250 | 11/1984 | Hirvonen et al. | 356/369 |
| 4,576,479 | 3/1986 | Downs | 356/351 |
| 4,585,348 | 4/1986 | Chastang et al. | 356/369 |
| 4,636,075 | 1/1987 | Knollenberg | 356/338 |
| 4,740,079 | 4/1988 | Koizumi et al. | 356/237 |

Primary Examiner—Richard A. Rosenberger
Attorney, Agent, or Firm—Robert E. Harris

[57] ABSTRACT

A surface analysis system and method are disclosed for determining particle contamination and/or defects on or below a surface of material. Laser beams having different polarizations are directed to the surface to be analyzed and light scattered from particle contamination and/or defects on or below the surface is collected and detected to provide electrical signals representative thereof. The electrical signals are then processed to provide an output indicative of sensed contamination and/or defects. In the embodiment particularly shown and described, a pair of polarized laser beams, one of which is a "P" polarized laser beam and the other of which is a "S" polarized laser beam, are separately directed to a monitoring region so that the beams impinge at a common point on the surface to be analyzed. The scattered light is then collected and split into two components depending upon whether scattered from the "P" polarized laser beam or the "S" polarized laser beam and each component is separately detected, after which the electrical outputs are processed to provide the desired indication.

21 Claims, 3 Drawing Sheets

*Fig_1A*

*Fig_1B*

*Fig_7*

Fig_2

Fig_3

Fig_4

Fig_5

Fig_6

SURFACE ANALYSIS SYSTEM AND METHOD

RELATED APPLICATION

This application is a continuation of U.S. patent application Ser. No. 06/859,054, filed May 2, 1986, and now abandoned.

FIELD OF THE INVENTION

This invention relates to a surface analysis system and, more particularly, relates to analysis of a surface to determine the presence of particle contamination and/or defects on or below the surface of a material.

BACKGROUND OF THE INVENTION

The use of optical detecting devices to determine the presence and/or size of particles is well known, and is shown, and such detecting devices have hertofore included lasers to provide the illuminating beam (see, for example, U.S. Pat. Nos. 3,406,289 and 4,571,079).

An optical surface scanning device, commonly referred to as a wafer scanner, has been heretofore utilized in semiconductor processing to identify surface adhering particulates. Semiconductor wafers are normally run through various manufacturing process steps (often as "virgin" wafer witness blanks) to determine the amount of contamination deposited on the wafer and assumed to be generated by the process. The process may be, for example, a photoresist coating process, a silicon oxide forming furnace operation, a photolithographic circuit masking process, or any of an array of others, but the wafer scanner has proved to be a useful tool to monitor any of them. Although independent techniques are also utilized to measure the microcontamination in various process fluids, the wafer scanner has nevertheless been utilized to provide monitoring where it directly effects the product, i.e., on the wafer itself.

As with any measuring tool, it is a fundamental requirement of apparatus measuring microcontamination to possess repeatability and accuracy. Repeatability or reproducibility must be inherent to achieve accuracy but places no guarantee of accuracy. Resolution implies an ability to separate measurement values of similar magnitude but again does not assure accuracy. Indeed, as with many types of instrumentation, the determination of performance with respect to resolution, repeatability, and accuracy can often be very difficult to assess and verify.

This proves to be the case with wafer scanners which appear to often generate an intolerable disparity of results when particles of known size were deposited on test wafer surfaces and analyzed. Considering that the contaminants are located in a thin plane (so that a shallow depth-of-field is required), the background light level is extremely low, and repetitive measurements are possible, it would appear that surface microcontamination measurements should be more easily accomplished than are aerosol measurements. However, aerosol instruments now known have far superior resolution than do now known wafer scanners.

A wafer scanner is, in reality, a fairly straightforward device, and three fundamental types of wafer scanners are generally known. In one, the wafer moves along a belt or other transport mechanism (usually stepper driven) and a laser beam is focused onto a small spot on the surface. The spot is dithered laterally by an oscillating mirror (or a rotating polygon), and the combination of the two motions generates a raster scan suitable for direct cathode ray tube display of coordinates illuminated on the wafer. The light reflected from the wafer is trapped or monitored for extinction, while the diffusely scattered light is analyzed for its bulk scattering (DC or low frequency changes in diffuse scattering) and point scattering events from particles or perhaps digs and scratches (AC or high frequency changes in diffuse scattering).

A second type of wafer scanner now generally known differs from the first above described type in that the wafer rotates on a chuck fixed to a transport stage, and light is incident and collected at fixed angles. The conversion of scanning polar coordinates to display cartesian coordinates can be accomplished easily in software or by electrical resolvers.

The third type of wafer scanner now known is the simplest optically. The wafer is totally illuminated by white light generated from a high intensity source such as an arc lamp. At an oblique angle, a vidicon (usually solid state) is positioned to view the wafer and particles appear directly on the vidicon output. This system is, however, the most complex in terms of analysis requiring post analysis of video data.

In all of the known wafer scanner systems, particles or defects are analyzed by measuring the amount of light scattered and compared to a calibration, or response, curve in a manner similar to most common aerosol or hydrosol counters.

Polystyrene latex microspheres (PSL) are the most desirable particle calibration material, although attempts have been made to generate defect patterns via microlithography to effect "calibration wafers". Particles cannot, however, now be simulated using pattern defects in any certain way, and the users and manufacturers of wafer scanners have found difficulty in using PSL particles as a preferred calibration material for a variety of reasons, including: PSL particles cannot be applied as a liquid suspension because no solvent is clean enough to evaporate without leaving a residue that could be confused with the PSL particles; application of dry PSL particles using standard aerosol nebulizing techniques require some other means of verifying that the particles would attach and "stick"; response sometimes appears to be a function of position; and the results generally appear nonmonotonic and thus ambiguous (i.e., smaller particles gave greater signals than larger ones). The last situation is one familiar to most researchers who have studied aerosol counters and most aerosol viewing geometries have to be tailored to achieve a monotonic response.

It is also the primary reason existing instruments have not adopted PSL as the calibration standard. Existing technology does not produce a monotonic calibration with uniform spherical particles.

As can be appreciated from the foregoing, an improved system and method could therefore be advantageously utilized for effecting analysis of the surface of an element to determine particle contamination and/or defects on or below the surface of a material.

SUMMARY OF THE INVENTION

This invention provides an improved system and method for analyzing the surface of a material. Beams having different polarizations are directed at the surface and light scattered therefrom is collected and detected to produce electrical signal outputs representative of sensed contamination or defects. In the particularly described embodiment, a "P" polarized laser beam and an "S" polarized laser beam are generated and separately directed to the surface at a common point, and light scattered from both is commonly collected and then separated to provide electrical signals representative thereof. The electrical signals are then processed to provide an output indicative of contamination and/or defects.

It is therefore an object of this invention to provide an improved system and method for surface analysis.

It is still another object of this invention to provide an improved system and method for surface analysis utilizing beams having different polarizations.

It is still another object of this invention to provide an improved system and method for surface analysis utilizing polarized beams one of which is a "P" polarized laser beam and the other of which is an "S" polarized laser beam.

It is still another object of this invention to provide an improved system and method for surface analysis for sensing particle contamination and/or defects on or below the surface of a material.

With these and other objects in view, which will become apparent to one skilled in the art as the description proceeds, this invention resides in the novel construction, combination, arrangement of parts, and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

To understand the advantages of this invention, it is necessary to have a physical understanding of the light scattering process using MIE theory to calculate scattering responses.

For a particle suspended in a homogeneous medium, a single incident plane wave generates a single outgoing spherical wave centered at the particle. However, a particle resting on a surface, while totally illuminated by an incoming (incident) wave, is also partially illuminated by an outgoing (reflected) wave. In addition, portions of the scattered waves propagating toward the surface are partially reflected by the surface and then partially rescattered by the particle (i.e., multiply scattered).

Figure 1A:
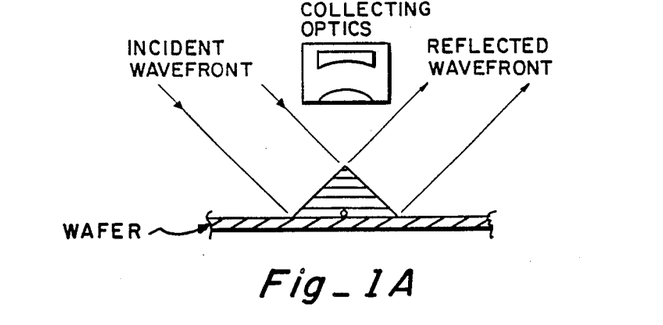
FIG. 1A is a simplified side view illustrating generation of standing waves in a region of overlapping wave fronts on a silicon wafer.
Figure 1B:
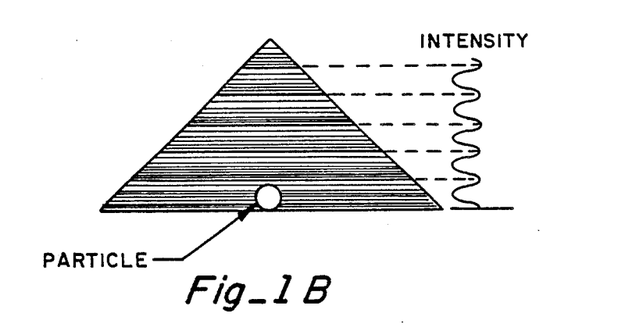
FIG. 1B is an expanded view of the overlapping wave fronts as shown in FIG. 1A.

All of the scattered wave components have permanent phase relationship and interfere in a complex manner. Of additional concern is that an interference zone is set up in the overlapping common volume, as shown in FIGS. 1A and 1B. The fringe contrast in this interference zone is a function of the amplitude of the reflected wave, while the fringe spacings depend on the angles of illumination (incidence angle $\theta_i$) and state of polarization of the incident wave. The fringe spacing is given by:

$$\text{fringe spacing} = \frac{\lambda}{2 \cos \theta_i}$$

The fringe zone represents a standing wave pattern which is phase-locked to the surface. For "S" polarization (electric field vector (E) perpendicular to the plane of incidence), there is a 180° phase shift, upon reflection, at all incidence angles for most surface materials, and thus the surface itself is generally in the first dark zone.

The contrast of the fringes (or the standing wave ratio (SWR)) is a function of the amplitude of the reflected wave which can be computed from material optical data. For silicon, the contrast is about 60% (SWR=2.5) for normal incidence and increases to 100% at grazing incidence.

For "P" polarization (E in the plane of incidence), it is necessary to resolve $E_p$ into its two orthogonal components: $E_p \parallel$ parallel to the surface and the other $E_p \perp$ perpendicular to the surface. $E_p \parallel$ undergoes a 180° phase shift, while the $E_p \perp$ has 0° phase shift until angles of incidence exceed Brewster's angle, whereupon a 180° phase shift again occurs.

Figure 2:
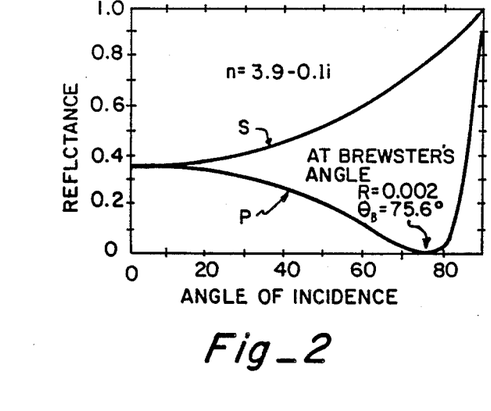
FIG. 2 is a graph illustrating reflectivity of silicon as a function of angle and polarization.

Thus, in general, for "P" polarization, the fringe zone is also phase locked on a dark zone for 0° incidence angles gradually shifting in phase and lowering in contrast as incidence angles increase. Amplitudes for the reflected "P" and "S" polarization components for silicon are shown in FIG. 2. Silicon, having a complex reflective index, does not have a zero reflectance at Brewster's angle. For silicon, the "P" fringe contrast decreases from 60% at normal incidence to nearly 0% at Brewster's angle where the standing waves essentially disappear.

The existence of standing waves phase-locked to a surface generates some interesting possibilities for scattering responses. One immediate result is that for normal incident waves, a very small ($<<\lambda$) particle attached to the surface would scatter very weakly as compared to a position elevated above the surface to a bright zone (in fact, nearly 4x less). At oblique incidence, a "P" wave would also scatter more than an "S" wave for such very small particles. Collecting geometries are, however, biased in favor of "S" collection because "S" scattering is greatest normal to the surface while "P" is greatest parallel to the surface. As particles increase in size, they extend into more than one fringe generating a complicated response.

Thus the amplitude of any reflected wave illuminating the particle is a function of the state of polarization of the incoming wave and the optical properties of the surface and must be accurately known to determine scattering response. However, for all but the smallest of particles, and at all but the largest of incidence angles, this reflected wave is itself attenuated by the particle's presence; the particle partially shadows the reflected beam.

Obviously, the problem would be simplified if the particle could be suspended several diameters above the reflective boundry to move the near-field away from the boundary. It must remembered, however, that the near-field varies as $I/D^{-2}$, and the offset need only be a few microns for the shadowing effect to be lost.

Figure 3:
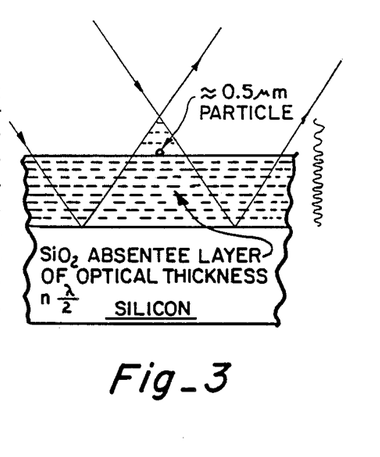
FIG. 3 is a simplified side view illustrating a particle raised several microns above a reflecting surface.

To this end, several $\lambda/2$ layers of $SiO_2$ can be grown on a silicon wafer to provide a situation such as shown in FIG. 3. For submicron particles, the effect of shadowing by the particle could then, for all practical purposes, be neglected. Tests have been conducted with monodisperse PSL particles elevated by such a stand-off-layer where good agreement between theoretical (using MIE theory) and empirical values were found.

If an odd multiple of $\lambda/4$ spacing is utilized, the results would obviously change as the particle transitions from a dark to a bright zone. Aside from the fact that the standoff-layer simplifies the theoretical treatment, it also hints at possible significant changes in response for patterned versus "virgin", or bare, wafers.

However, the case of greatest interest is that of FIG. 1 corresponding to a bare wafer and the strengths of the reflected wave must be reasonably estimated if a useful representation of the response is to be obtained. The reason for this concern is apparent when it is realized that the incident beam results in a direct "collectable" backscattered contribution while the reflected wave generates a direct "collectable" forward scattered component. The forward scatter is substantially greater than the backscatter for all but Rayleigh sized particles, in which case they are equal. It is therefore apparent that the reflected wave's amplitude must be determined quite accurately. In addition, phase differences between all components must be determined to compute scattered intensities.

When a particle is very small, its effective scattering cross section is much less than its geometric cross section, and thus the effect that the particle has on the reflected wave can be neglected. However, as the particle approaches the wavelength in size, its scattering cross section becomes greater than its geometric cross section ($Q_{sc}>1$, where $$Q_{sc} = \frac{\text{scattering cross section}}{\text{geometric cross section}}),$$

and the presence of the particle greatly effects the reflected wave. At 0° incidence, the reflected wave is not effectively illuminating particles with $Q_{sc}>1$ corresponding to sizes larger than $\lambda$; its existence being precluded by the particle itself. Thus, for such sizes at incidence angles near 0°, the scattering that results is closely approximated by backscatter only. Only when the particle diminishes in size to where $Q_{sc}<1$, or for larger incidence angles, can a reflected component begin to exist and generate measurable forward scatter.

Figure 4:
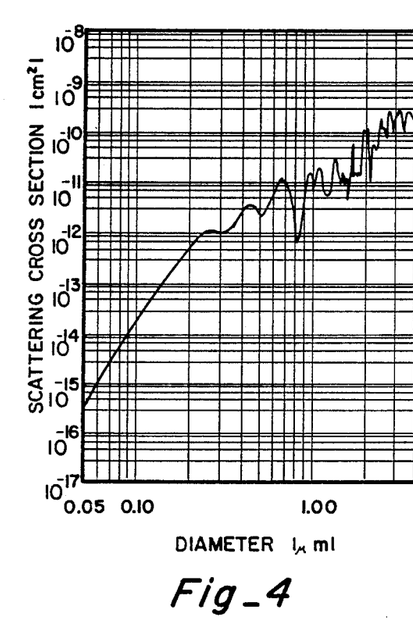
FIG. 4 is a graph illustrating the scattering cross-sections for PSL on silicon at 0° angle of inclination.

For computation purposes, the reflected component generated (that portion potentially shadowed) was attenuated by reducing its amplitude in proportion to the particle's scattering efficiency factor. At this point, it could be seen that a compensating factor emerged which reduced dynamic range—as size increased to where strong forward scatter was dominant, it was the least likely to be generated. Theoretical values for bare silicon at 0° incidence angles and for ±5° collecting angles are shown in FIG. 4. Computations for sizes larger than 1 $\mu$m are subject to increasing error, and while the mean trends are useful, the response oscillatory signatures are not exactly correct in phase and amplitude. However, the computed response in the submicron range is indistinguishable from actual measurements. For sizes larger than 1 $\mu$m, the means response is essentially a $D^2$ function. Clearly, this geometry generates an ambiguous response over much of the size range.

Figure 5:
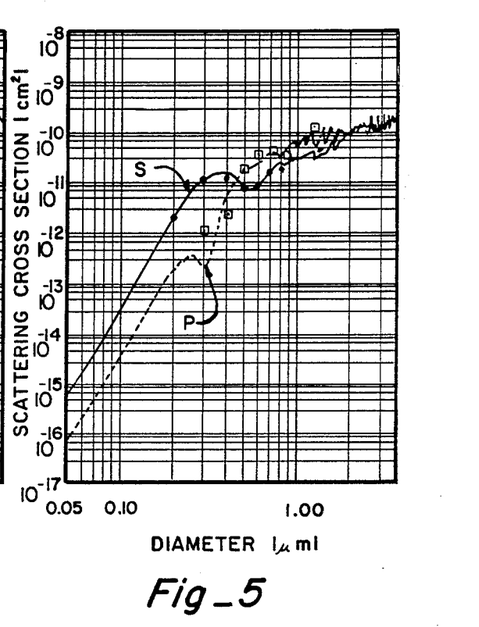
FIG. 5 is a graph illustrating the scattering cross-sections of PSL on silicon at 60° angle of inclination.

For polarization effects, the case of 60° incidence angle can be examined. Here, it is a situation where the particle cannot alternate much of the reflected illumination since a large portion of it is generated by reflection well outside the region influenced by the particle. Again, for very small particles, it is illuminated by an unperturbed reflected wave, but as size increases, there is again some small attenuation of the reflected component which is again estimated from $Q_{sc}$. The results for both "S" and "P" polarization at 60° incidence angles and ±10° collecting angles are shown in FIG. 5, along with experimental values for PSL. The agreements are seen to be quite good in the important submicron range of sizes.

The results of FIG. 5 might at first appear to be as difficult to utilize as those of FIG. 4. However, if scattering from both polarization measurements are independently analyzed there are two calibration relationships from which to choose, and also there is a polarization ratio available. For example, for the case of FIG. 5, it is possible to develop a monotonic calibration which is effected by using the "S" polarization response for sizes up to about 0.4 $\mu$m and then switching to "P" polarization responses for sizes larger than 0.4$\mu$m. This type of "polarization diversity" is utilized in the schematic of the invention shown in FIG. 6.

Figure 6:
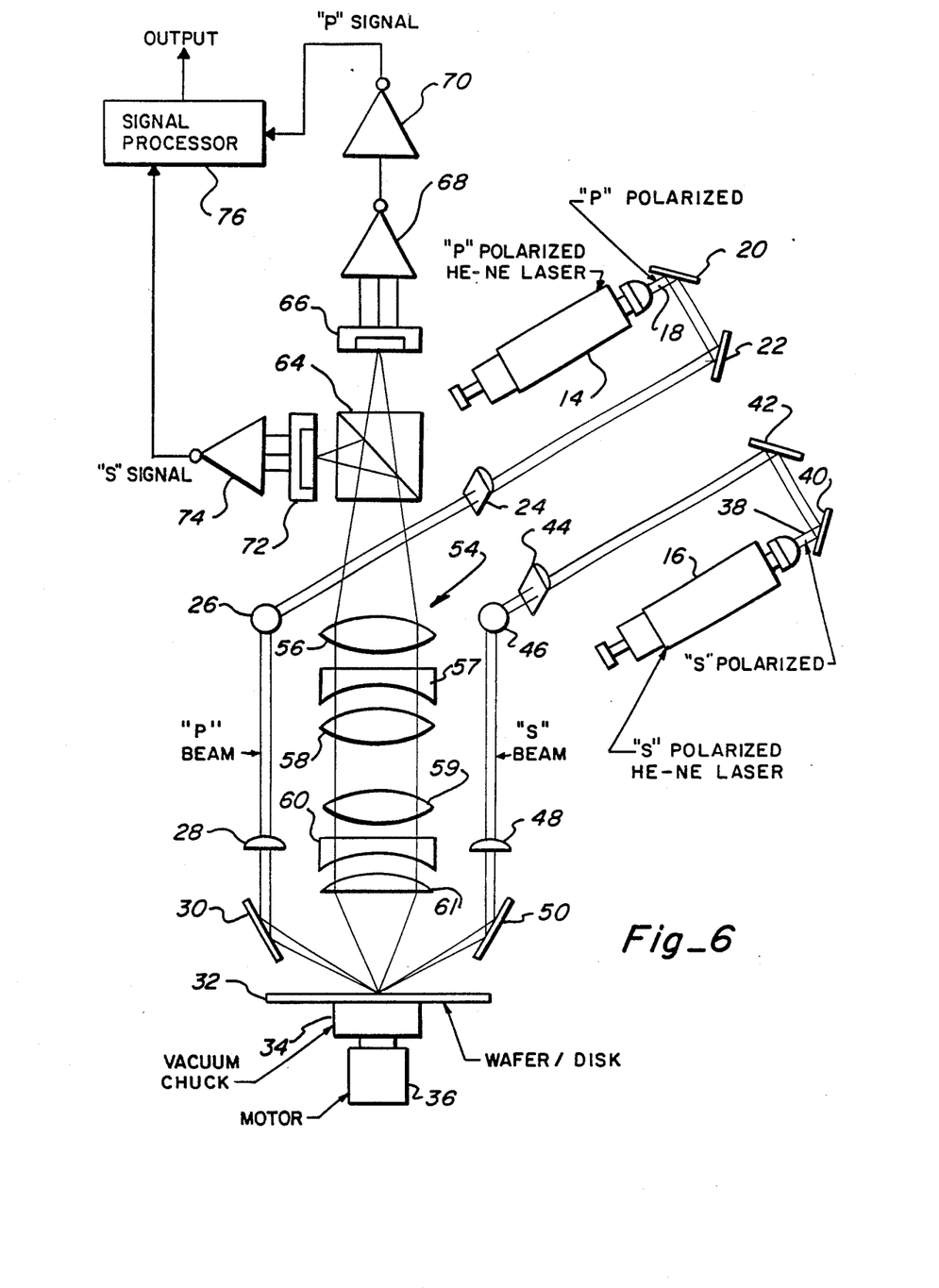
FIG. 6 is a schematic illustrating the system of this invention.

As shown in FIG. 6, "P" polarized He-Ne laser 14 is utilized, as is an "S" polalrized He-Ne laser 16. While not specifically shown, the lasers could also operate at different frequencies as well as having different polarizations. As shown, the "P" polarized beam 18 from laser 14 is reflected by mirrors 20 and 22, coupled through cylindrical lens 24, reflected by mirror 26, coupled through cylindrical lens 28, and reflected by mirror 30, which directs the beam to a point (monitoring region) on the surface of wafer-disk 32.

As also shown in FIG. 6, wafer-disk 32 is supported on vacuum chuck 34 so that the surface is at the monitoring region and the chuck is rotated, in conventional manner, by motor 36.

The "S" polarized beam 38 from laser 16 is refleted by mirrors 40 and 42, coupled through cylindrical lens 44, reflected by mirror 46, coupled through cylindrical lens 48, and reflected by mirror 50, which mirror directs are "S" beam to the surface of wafer-disk 32 so that the two beams impinge the surface at a common point at the monitoring region.

Light scattered due to particle contamination and/or surface defects is collected through lens arrangement 54, which includes a six element diffraction limited dark-field objective lens set 56, 57, 58, 59, 60 and 61, with the output from the lenses being directed to and through polarizing beam splitter 64. Polarizing beam splitter 64 separated or divides the scattered light into two components, one of which is representative of light scattered from the "P" beam and the other of which is representative of light scattered from the "S" beam. The component containing the light scattered from the "P" beam is directed through the beam splitter to detector 66 where scattered light is detected and representative electrical signals generated, which signals are then coupled through amplifiers 68 and 70 to provide a "P" signal output. The "S" beam component is directed from the beam splitter to detector 72 where the light sensed is utilized to form electrical signals representative thereof, which electrical signals are than coupled through amplifier 74 to provide an "S" signal output.

If the lasers have different frequencies, the polarizing beamsplitter 64 can be replaced with a dichroic (color-separating) beamsplitter or otherwise split and filtered to separate the two scattering signals. The "S" and "P" beams will thus be of different color (frequency).

As also indicated in FIG. 6, the outputs from amplifiers 70 and 74 are coupled to signal processor unit 76 which provides an output indicative of particle contamination and/or defects on and below the surface of the material. This output can be a monotonic output indicative of particle contamination sensed. For such an output, processing unit 76 may include switching means to accept process "S" polarization signals for particle sizes up to about 0.4 $\mu$m and "P" polarization signals for particle sizes over 0.4 $\mu$m.

Figure 7:
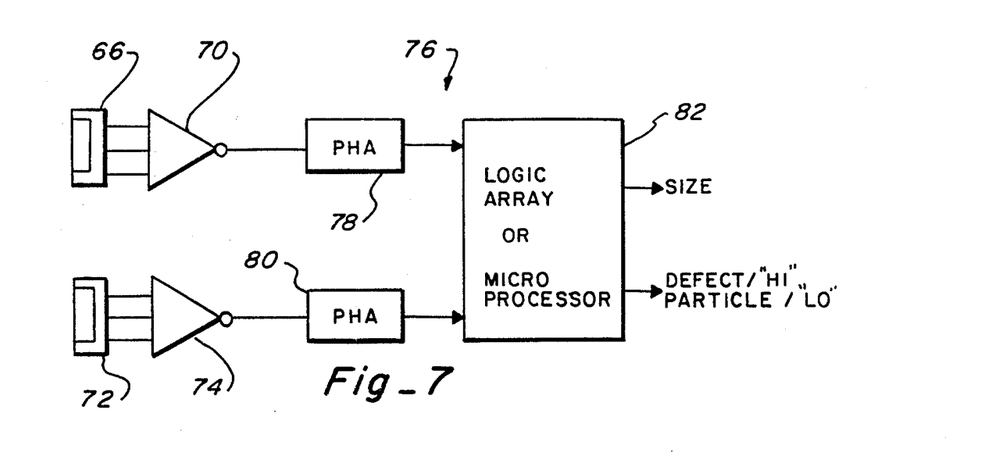
FIG. 7 is a schematic illustrating the processing unit shown in FIG. 6.

Processing unit 76 is shown in greater detail in FIG. 7. As shown, unit 76 includes pulse height analyzers 78 and 80 connected to receive the outputs from amplifiers 70 and 74, with outputs from analyzers 78 and 80 being coupled to logic array or microprocessor 82. The analysis of the "S" and "P" signals is accomplished with the two independent pulse height analyzers 78 and 80. The measured scattering amplitudes generated by PHA's 78 and 80 are conveniently compared using unit 80 which can include preprogrammed logic arrays or via a "lookup" table using microprocessor based software to interpret the measured values and make decisions as to size or distinguish particles from surface defects.

A second use of polarization analysis is for surface defects. Surface defects in general, do not exhibit polarization sensitivity nearly to the extent that small particles do. All of the scattering occurs at one plane without the complicating effects of illumination by multiple beams. The primary effect is that of diffuse scattering by a small localized area. The scattering for "S" polarization versus "P" polarization is generally a constant for a particular viewing solid angle and does not reverse response magnitude with changing size as particles do. Particles can thus be distinguished from surface defects by polarization ratio measurements except at the size where polarization ratio or particles and defects are equal.

For other collecting angles, the response functions will differ, but in general, the "S" polarization will provide higher scattering response than "P" for smaller submicron sizes with the S/P ratio reversing as size increases. It is also possible to use a single laser which provides both controlled "S" and "P" outputs or circularly or elliptically polarized outputs.

As can be appreciated from the foregoing, this invention provides an improved surface analysis system and method that is well suited for determining particle contamination and/or defects on or below the surface of a material.

What is claimed is:

1. A surface analysis system, comprising:
   beam generating means for providing first and second illuminating beams having predetermined different polarizations;
   beam directing means for directing said beams to a monitoring region;
   support means for supporting a material having a surface to be analyzed for the presence of submicron particles on and below said surface with said surface being positioned at said monitoring region so that said beams impinge on said surface in a manner such that light is scattered by contamination and defects on and below said surface due to the presence of said submicron particles;
   collecting means for collecting intensities of said light scattered by said contamination and defects on and below said surface;
   separating means for separating said intensities of scattered light collected by said collecting means into first and second components with said first component including intensities of scattered light from said first beam and said second component including intensities of scattered light from said second beam;
   first and second detecting means, said first detecting means receiving said first component of scattered light intensities from said separating means and said second detecting means receiving said second component of scattered light intensities from said separating means, said first and second detecting means, responsive to receipt of said components of scattered light intensities, providing separate outputs indicative thereof; and
   processing means for receiving said outputs from said detecting means and utilizing the same to provide an output indicative of said submicron particles on and below said surface.

2. The system of claim 1 wherein said beam generating means includes first and second lasers providing laser outputs having different said polarizations.

3. The system of claim 2 wherein said first laser provides a "P" polarized beam and said second laser provides an "S" polarized beam.

4. The system of claim 3 wherein said separating means includes a polarizing beam splitter for separating light intensities scattered from said "P" polarized beam and said "S" polarized beam.

5. The system of claim 1 wherein said beam generating means includes a single laser that provides one of "S" and "P" polarized beams, circularly polarized beams, and elliptically polarized beams, and wherein said separating means includes means for separating said light intensities scattered by said contamination and defects on and below said surface when impinged on by the particular beam selected.

6. The system of claim 1 wherein said support means includes a chuck having said material positioned thereon, and wherein said system includes a motor for rotating said chuck for scanning of said surface to be analyzed.

7. The system of claim 1 wherein said collecting means includes a diffraction limited dark-field objective lens set for collecting said scattered light intensities.

8. The system of claim 1 wherein said processing means provides an output indicative of at least one of contamination and defects on and below said surface.

9. The system of claim 8 wherein said processing means includes means for determining ratio measurements of detected scattered light to enable distinguishing of particle contamination from defects on and below said surface.

10. A surface analysis system, comprising:

laser means for providing first and second beams having different polarizations;

beam directing means including an arrangement of mirrors and lenses for directing said first and second polarized beams to a monitoring region at substantially identical incidence angles;

support means for supporting a material having a surface to be analyzed for the presence of submicron particles on and below said surface with said surface being positioned at said monitoring region so that said beams impinge on said surface in a manner such that light is scattered by contamination and defects on and below said surface due to the presence of said submicron particles;

collecting means including a lens set for commonly collecting said light scattered by said contamination and defects on and below said surface;

polarizing beam splitting means for separating said collected light scattered from said first beam from said collected light scattered from said second beam;

detecting means for separating received collected light scattered from each of said beams and responsive thereto providing outputs indicative thereof; and processing means for receiving said outputs from said detecting means and utilizing the same to provide an output indicative of said submicron particles on and below said surface.

11. The system of claim 10 wherein said laser means includes a first laser providing a "P" polarized beam and a second laser providing an "S" polarized beam.

12. The system of claim 10 wherein said processing means provides an output indicative of at least one of said contamination and defects on and below said surface.

13. A surface analysis system, comprising:

support means for supporting a material having a surface to be analyzed by light scattering for the presence of submicron particles on and below said surface with said surface being maintained at a monitoring region in a manner such that light is scattered by contamination and defects on and below said surface due to the presence of said submicron particles;

first laser means providing a "P" polarized laser beam;

second laser means providing an "S" polarized laser beam;

first directing means for directing said "P" polarized laser beam to said monitoring region at a predetermined incidence angle;

second directing means for directing said "S" polarized laser beam to said monitoring region at said predetermined incidence angle so that "P" polarized laser beam and said "S" polarized laser beam impinge on said surface at substantially a common point;

collecting means including a lens set for commonly collecting said light scattered from on and below said surface due to the presence of submicron particles with respect to both said "P" polarized laser beam and said "S" polarized laser beam;

polarizing beam splitting means for separating said light scattered from "P" polarized laser beam and said "S" polarized laser beam;

first detecting means for receiving said light scattered from said "P" polarized laser beam and providing an electrical signal indicative thereof;

second detecting means for receiving said light scattered from said "S" polarized laser beam and providing electrical signal indicative thereof; and signal processing means connected to receive the outputs from said first and second detecting means and responsive thereto providing an output indicative of submicron particles on and below said surface to thereby indicate at least one of contamination and defects on and below said surface of said material.

14. The system of claim 13 wherein said processing means provides a monotonic output indicative of particle contamination sensed in and at said surface.

15. A method for analyzing the surface of an element, said method comprising:

providing a first polarized beam;

providing a second polarized beam having a polarization different from said first beam;

directing said first and second beams to a monitoring region at substantially identical incidence angles;

providing a material at said monitoring region with said material having a surface to be analyzed by light scattering for the presence of submicron particles on and below said surface with said surface being positioned at said monitoring region so that said beams impinge on said surface in a manner such that light is scattered by contamination and defects on and below said surface due to the presence of said submicron particles;

collecting intensities of said light from said first and second beams that have been scattered by contamination and defects on and below said surface of said material due to the presence of said submicron particles;

separating said collected light intensities scattered from said first and second beams;

detecting said separated and collected light intensities scattered from first and second beams to form electrical signals indicative thereof; and processing said electrical signals to provide an indication of submicron particles to thereby indicate at least one of contamination and defects on and below said surface of said material.

16. The method of claim 15 wherein said step of providing said first and second beams includes providing first and second laser beams, said first laser beam having a "P" polarization and said second laser beam having an "S" polarization.

17. The method of claim 15 wherein said step of processing said electrical signals includes providing an indication of submicron particles having sizes at least as small as 0.4 microns.

18. The method of claim 15 wherein said method includes utilizing light intensities scattered from said "P" polarized beam for analysis of particle sizes up to about 0.4 microns and utilizing said light intensities scattered from said "S" polarized beam for analysis of particle sizes above about 0.4 microns.

19. The method of claim 15 wherein said method includes determining ratio measurements of detected scattered light intensities to enable distinguishing of contamination from defects on and below said surface.

20. The method of claim 15 wherein said step of detecting said separated and collected light intensities includes separately detecting light intensities scattered from said first and second beams and providing separate outputs each indicative of a different one of said detected light intensities to said processing means.

21. A surface analysis system, comprising:

beam generating means for providing first and second illuminating beam having predetermined distinguishing beam characteristics;

beam directing means for directing said beams to a monitoring region;

support means for supporting a material having a surface to be analyzed for the presence of submicron particles on and below said surface with said surface being positioned at said monitoring region so that said beams impinge on said surface in a manner such that light is scattered by contamination and defects on and below said surface due to the presence of said submicron particles;

collecting means for collecting intensities of said light scattered by said contamination and defects on and below said surface;

separating means for separating said intensities of scattered light collected by said collecting means into first and second components with said first component including intensities of scattered light from said first beam and said second component including intensities of scattered light from said second beam;

detecting means for receiving said scattered light intensities from said separating means and responsive thereto providing outputs indicative thereof; and processing means for receiving said outputs from said detecting means and utilizing the same to provide an output indicative of said submicron particles on and below said surface with said processing means having the capability of providing an output indicative of submicron particles having sizes at least as small as about 0.4 μm.

* * * * *

REEXAMINATION CERTIFICATE (1819th)
United States Patent [19]
Knollenberg

[11] B1 4,893,932
[45] Certificate Issued Oct. 20, 1992

[54] SURFACE ANALYSIS SYSTEM AND METHOD

[75] Inventor: Robert G. Knollenberg, Boulder, Colo.

[73] Assignee: Particle Measuring Systems, Inc., Boulder, Colo.

Reexamination Request:
No. 90/002,468, Oct. 7, 1991

Reexamination Certificate for:
Patent No.: 4,893,932
Issued: Jan. 16, 1990
Appl. No.: 262,216
Filed: Oct. 21, 1988

Related U.S. Application Data

[63] Continuation of Ser. No. 859,054, May 2, 1986, abandoned.

[51] Int. Cl.⁵ .............................................. G01N 21/01
[52] U.S. Cl. .................................... 356/369; 356/237; 356/338
[58] Field of Search ........................ 356/369, 338, 237

[56] References Cited

U.S. PATENT DOCUMENTS

| | | |
|---|---|---|
| 4,314,763 | 2/1982 | Steigmeier et al. |
| 4,391,524 | 7/1983 | Steigmeier et al. |
| 4,526,468 | 7/1985 | Steigmeier et al. |
| 4,576,479 | 3/1986 | Downs |
| 4,585,348 | 4/1986 | Chastang et al. |
| 4,598,997 | 7/1986 | Steigmeier et al. |
| 4,740,079 | 4/1988 | Koizumi et al. |

OTHER PUBLICATIONS

Optical Scanner of Dust & Defect Detection; Steigmeier & Auderset: RCA Review: vol. 44 Mar. 1983.
Letter of Mr. William Hug of Omnichrome, Inc. of Chino, Calif. Jul. 17, 1991.
Model Change Report Nov. 1978 for the RCA SC-2 Scanner for Defect & Dust Detection on Si Wafers.
Structural Perfection Testing of Films and Wafers by means of Optical Scanner—Steigmeier & Auderset—Laboratories RCA Limited Journal of the Electrochemical Society; vol. 131, No. 7, Jul. 1984.
Elastic Light Scattering Techniques for Semiconductor Technology—Steigmeier & Auderset—RCA Review; vol. 46; Mar. 1985.

*Primary Examiner*—R. A. Rosenberger

[57] ABSTRACT

A surface analysis system and method are disclosed for determining particle contamination and/or defects on or below a surface of material. Laser beams having different polarizations are directed to the surface to be analyzed and light scattered from particle contamination and/or defects on or below the surface is collected and detected to provide electrical signals representative thereof. The electrical signals are then processed to provide an output indicative of sensed contamination and/or defects. In the embodiment particularly shown and described, a pair of polarized laser beams, one of which is a "P" polarized laser beam and the other of which is a "S" polarized laser beam, are separately directed to a monitoring region so that the beams impinge at a common point on the surface to be analyzed. The scattered light is then collected and split into two components depending upon whether scattered from the "P" polarized laser beam or the "S" polarized laser beam and each component is separately detected, after which the electrical outputs are processed to provide the desired indication.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The Patentability of claims 10–20 is confirmed.

Claims 1 and 21 are determined to be patentable as amended.

Claims 2–9, dependent on an amended claim, are determined to be patentable.

1. A surface analysis system, comprising:
   beam generating means for providing first and second illuminating beams having predetermined different polarizations;
   beam directing means for directing said beams to a monitoring region;
   support means for supporting a material having a surface to be analyzed for the presence of submicron particles on and below said surface with said surface being positioned at said monitoring region so that said beams impinge on said surface in a manner such that light is scattered by contamination and defects on and below said surface due to the presence of said submicron particles;
   collecting means for collecting intensities of said light scattered by said contamination and defects on and below said surface;
   *polarization* separating means for separating said intensities of scattered light collected by said collecting means into first and second components with said *intensities of said first component having a different polarization than is included in said intensities of said second component, said* first component [including] *having* intensities of scattered light from said first beam and said second component [including] *having* intensities of scattered light from said second beam;
   first and second detecting means, said first detecting means receiving said first component of scattered light intensities from said separating means and said second detecting means receiving said second component of scattered light intensities from said separating means, said first and second detecting means, responsive to receipt of said components of scattered light intensities, providing separate outputs indicative thereof; and
   processing means for receiving said outputs from said detecting means and utilizing the same to provide an output indicative of said submicron particles on and below said surface.

21. A surface analysis system, comprising:
    beam generating means for providing first and second illuminating [beam] *beams* having predetermined distinguishing *polarization* beam characteristics;
    beam directing means for directing said beams to a monitoring region;
    support means for supporting a material having a surface to be analyzed for the presence of submicron particles on and below said surface with said surface being positioned at said monitoring region so that said beams impinge on said surface in a manner such that light is scattered by contamination and defects on and below said surface due to the presence of said submicron particles;
    collecting means for collecting intensities of said light scattered by said contamination and defects on and below said surface;
    *polarization* separating means for separating said intensities of scattered light collected by said collecting means into first and second components with said *intensities of said first component having a different distinguishing polarization beam characteristic than is included in said intensities of said second component, said* first component [including] *having* intensities of scattered light from said first beam and said second component [including] *having* intensities of scattered light from said second beam;
    detecting means for receiving said scattered light intensities from said separating means and responsive thereto providing outputs indicative thereof; and
    processing means for receiving said outputs from said detecting means and utilizing the same to provide an output indicative of said submicron particles on and below said surface with said processing means having the capability of providing an output indicative of submicron particles having sizes at least as small as about 0.4 $\mu$m.

* * * * *